United States Patent [19]

Hagiwara et al.

[11] Patent Number: 5,093,261
[45] Date of Patent: Mar. 3, 1992

[54] CANCER-RELATED ANTIGEN-SPECIFIC HUMAN IMMUNOGLOBULINS AND HUMAN/HUMAN HYBRIDOMAS HAVING THE ABILITY TO PRODUCE SAID HUMAN IMMUNOGLOBULINS

[75] Inventors: Hideaki Hagiwara, 1556, Kou, Befu-cho, Kasai-shi, Hyogo-ken; Junzo Nagao, Kasai, both of Japan

[73] Assignees: Yoshihide Hagiwara; Hideaki Hagiwara, both of Kasai, Japan

[21] Appl. No.: 196,610

[22] Filed: May 20, 1988

[30] Foreign Application Priority Data

May 23, 1987 [JP] Japan .................. 62-126687

[51] Int. Cl.$^5$ ............................. C12N 5/00
[52] U.S. Cl. .................. 435/240.27; 435/70.2; 435/70.21; 435/172.2; 435/240.21; 530/386; 530/388.15; 530/388.8; 530/861; 935/99; 935/100
[58] Field of Search ............. 435/240.27, 70.2, 70.21, 435/240.21, 172.2; 530/386, 387; 436/548; 935/99, 100

[56] References Cited

U.S. PATENT DOCUMENTS

| | | | |
|---|---|---|---|
| 4,693,975 | 9/1987 | Kozbor et al. | 435/240.27 |
| 4,761,377 | 8/1988 | Glassy et al. | 435/240.27 |
| 4,942,123 | 7/1990 | Lee et al. | 530/352 |
| 5,618,577 | 10/1986 | Handley et al. | 435/7 |

FOREIGN PATENT DOCUMENTS 0171083 12/1986 European Pat. Off. .
0222360 5/1987 European Pat. Off. .

OTHER PUBLICATIONS

Olsson et al. "Human-Human Hybridoma...", Human Hybridomas & Monoclonal Antibodies pp. 227-242, 1985 (Plemum Press).

Primary Examiner—Howard T. Mars
Assistant Examiner—Jessica H. Nguyen
Attorney, Agent, or Firm—Sherman and Shalloway

[57] ABSTRACT

A new human/human fused cell clone derived from human B cells having the ability to produce immunoglobulins and human B cells substantially lacking the ability to produce immunoglobulins, antigen-specific human immunoglobulins produced by the human/human fused cell clone, and a method of producing the human immunoglobulins. More specifically, a human/human hybridoma having the ability to produce antigen-specific human immunoglobulins, which is a human/human fused cell strain derived from human B cells of a human patient with liver cancer and a subclone of a human lymphoblast cell strain; and antigen-specific human immunoglobulins produced by the human/human fused cell strain.

7 Claims, No Drawings

CANCER-RELATED ANTIGEN-SPECIFIC HUMAN IMMUNOGLOBULINS AND HUMAN/HUMAN HYBRIDOMAS HAVING THE ABILITY TO PRODUCE SAID HUMAN IMMUNOGLOBULINS

This invention relates to a new human/human fused cell clone derived from human B cells having the ability to produce immunoglobulins and human B cells substantially lacking the ability to produce immunoglobulins, antigen-specific human immunoglobulins produced by the human/human fused cell clone, and to a method of producing the human immunoglobulins. More specifically, this invention relates to a human/human hybridoma having the ability to produce antigen-specific human immunoglobulins, which is a human/human fused cell strain derived from human B cells of a human patient with liver cancer and a subclone of a human lymphoblast cell strain. The invention also relates to antigen-specific human immunoglobulins produced by the human/human fused cell strain.

The invention also pertains to a method of producing antigen-specific human immunoglobulins which comprises cultivating the human/human fused cell strain in a culture medium, and isolating the antigen-specific human immunoglobulins from the culture broth.

The antigen-specific immunoglobulins are useful in medical, pharmaceutical and biochemical fields, for example for prevention, treatment and diagnosis of human liver cancer, the preparation of biochemical reagents and biopolymers, and purification of cancer antigens.

It was previously reported that mouse B cells sensitized with cancer or other antigens and mouse B cells from a mouse with myeloma were fused outside the mouse's body to produce mouse/mouse fused cells having the ability to produce mouse immunoglobulins specific to the above antigens and self-replicability [for example, "Koehler G. and Milstein C.: Nature, 256, 495 (1975) and Dippold, E. G., Lloyd, K. O., Li, L. T. C., Ikeda, H., Oettgen, H. F. and Old, L. J.: Proc. Nat. Acad. Sci., U.S.A., 77,6614(1980)].

It was also reported that human B-cells sensitized with an antigen and mouse B cells from a mouse with myeloma were fused outside the body to produce human/mouse fused cells having the ability to produce human immunoglobulins specific to the antigen and self-replicability [for example, Schlom, J., Wenderrich, P., and Teramoto, Y. A.: Proc. Nat. Acad. Sci., U.S.A., 77 (11), 6841 (1984)].

However, in the later attempt to obtain fused cells having the ability to produce immunoglobulins, loss of chromosomes occurs with time, and the ability of the fused cells to produce human immunoglobulins is lost with time. Thus, the fused cells obtained by the latter attempt have the serious defect that their ability to produce immunoglobulins is very unstable.

As an attempt to form human/human fused cells having the ability to produce human immunoglobulins, it was reported that human B cells sensitized with measles virus or hapten (2,4-dinitrophenyl) were used as a donor and fused outside the body with a cell line (human B cell, parent cell line) having the ability to produce human immunoglobulins taken from a patient with myeloma to produce human/human cells having the ability to produce human immunoglobulins specific to the above antigen and self-replicability [for example, Croce, C. M., Linnenbach, A., Hall, W., Steplowski, Z., and Koprowski, H.: Nature, 288, 488 (1980), and Olsson, L. and Kaplan, H. S.: Proc. Nat. Acad. Sci., U.S.A., 7 (9), 5429 (1980)].

The mouse/mouse hydbridoma obtained by the above method can produce only mouse immunoglobulins. When the mouse/human hybridoma is cultivated, the formation of products derived from the mice inevitably form in the culture, and with loss of human chromosomes, the hybridoma may lose the ability to produce human immunoglobulins. For this reason, it is desired to produce human immunoglobulins from the human/human fused cells. The above-cited papers reporting human immunoglobulins produced from the human/human hybridoma do not show any proof of the bindability of the immunoglobulins to cancer cells. In particular, these papers fail to describe anything on the bindability of the immunoglobulins to liver cancer cells and liver cancer tissues.

One of the inventors of the present application created a human/human hybridoma which is a human/human fused cell derived from human B cell taken from a human patient with cervical cancer of the uterus and a subclone of a human lymphoblast cell strain and which has the ability to produce antigen-specific human immunoglobulin (Japanese Laid-Open Patent Publication No. 137497/1984). This patent document discloses that the human immuloglobulin produced by the hybridoma showed a stronger power of binding to cervical epitheloid carcinoma cells and cell lines Hela and Caski derived from the above cells than to normal fibroblast cells (Wl-38). It, however, fails to refer to its bindability to human liver cancer cells and human liver cancer tissues.

Japanese Laid-Open Patent Publication No. 44900/1986 (European Laid-Open Patent Publication No. 171083) described a monoclonal antibody which specifically reacts with antigens related to pancreas cancer, colon cancer and liver cancer, and states that fused cells for producing the monoclonal antibody are obtained by fusion of antibody-producing cells with bone marrow cells which are preferably derived from animals of the same species. This patent document specifically discloses only a mouse/mouse fused cell strain.

Japanese Laid-Open Patent Publications Nos. 167699/1986 and 36398/1987 give statements on monoclonal antibodies which specifically react with esophagus cancer, lung cancer, stomach cancer and liver cancer, and fused cells capable of producing the monoclonal antibodies are obtained by fusion of antibody-producing cells with myeloma cells. These patent document specifically disclose only mouse/mouse fused cell lines. The patent documents only show the bindability of the monoclonal antibodies produced by mouse/mouse fused cells to human liver cancer cells (HEK) as a specific example of bindability to liver cancer cells. They fail to refer to bindability to other liver cancer cells or human liver cancer tissues. They show nothing on monoclonal antibodies produced by human/human hybridomas and their bindability to liver cancer cells or tissues.

The present inventors have made investigations to produce human/human hybridomas, and have succeeded in creating human/human hybridoma which is a human/human fused cell derived from human B cells of a human patient with liver cancer and a subclone of human lymphoblast cells, and which has the ability to produce antigen-specific human immunoglobulins.

The present inventors found that one of such human/human hybridomas has the immunological characters of the human B cells of the human liver cancer patient and can continue to have these characters stably, and that the above human/human hybridoma has the ability to produce human immunoglobulin A (IgA) and the produced antibody is an antigen-specific monoclonal antibody showing bindability to human liver cancer cells. They also successfully produced such antigen-specific human immunoglobulins.

The present inventors also found that the new human/human hybridoma described above can be produced by fusing a group of human cells containing human B cells taken from a human patient with liver cancer with a group of human cells containing a subclone (human B cells) of human lymphoblast cells outside the human body to produce fused cells of the human B cells and the human B cells, cultivating the fused cells in a customary manner in HATO medium, and isolating the fused cell clone. They succeeded in creating the above human/human hybridoma (for example, TOH/B9) by the above method.

Furthermore, the present inventors found that another type of the human/human hybridoma has the immunological characters of the human B cells from the human liver cancer patient and can continue to have such characters stably; that the above human/human hybridoma has the ability to produce human immunoglobulins G (IgG); and that these antibodies are antigen-specific monoclonal antibodies which show bindability to human liver cancer cells and a slice of human liver cancer tissue obtained by fixing it with formalin and then embedding it in paraffin. They also succeeded in producing such antigen-specific human immunoglobulins.

The present inventors also found that the above new type of human/human hybridomas can be produced by fusing a group of human cells containing human B cells taken from a patient with liver cancer with a group of human cells containing a subclone (human B cells) of human lymphoblast cells (human B cells) outside the human body to form fused cells, cultivating the fused cells in a customary manner in a HATO medium, and isolating the fused cell clone, and succeeded in creating the above human/human hybridomas (for example, TOH/D5) by the above method.

It is an object of this invention therefore to provide human/human hybridomas which are human/human fused cells derived from human B cells taken from a human patient with liver cancer and a subclone (human B cells) of human lymphoblast cells and which have the ability to produce antigen-specific human immunoglobulins.

Another object of this invention is to provide a method of producing human immunoglobulins (monoclonal antibodies) specific to cancer-related antigens showing bindability to human liver cancer cells or human liver cancer tissues using the above human/human hybridomas.

The above and other objects of the invention along with its advantages will become more apparent from the following description.

The human/human hybridomas of this invention are human/human fused cells derived from human B cells which can be obtained from the blood, lymph node, spleen, bone marrow, etc. of a human patient with liver cancer and a subclone (human B cells) of human lymphoblast cells, for example HIH/TO1 (FERM BP-1884) and have the ability to produce antigen-specific human immunoglobulins (monoclonal antibodies) which show bindability to human liver cancer cells or human liver cancer tissues.

The present inventors have, for the first time, produced human/human hybridomas having the ability to produce human immunoglobulins binding specifically to cancer-related antigens such as liver cancer by fusing human B cells of a human patient with liver cancer with a subclone (human B cells) of lymphoblast cells substantially lacking the ability to produce immunoglobulins.

The fusing operation for producing the fused cells may be carried out by any known method. For example, it is carried out by contacting the human B cells of the human liver cancer patient with the subclone of human lymphoblast cells in the presence of a fusion promoter in a solvent.

Prior to the fusion operation, it is desirable to subject the human B cells of the human liver cancer patient to a preliminary cultivation treatment in the presence of a human B cell growth factor (human BCGF) and an anti-human IgM antibody (anti-$\mu$). The preliminary cultivation treatment may, for example, be carried out by utilizing a suitable basal medium containing the human BCGF and anti-$\mu$ or its modified medium in an atmosphere containing 5% $CO_2$ at a temperature of about 30° C.±3° C. for about 5 to 7 days. Known basal media or modified media thereof exemplified, for example, in Japanese Laid-Open Patent Publication No. 51983/1987 may be used as the basal or modified medium. The culture media may contain other known growth factors, amino acids, vitamins, minerals, sugars, coenzymes and fatty acids, for example. The human BCGF and anti-$\mu$ are commercially available, and methods for their preparation are known. For the former, see, for example, Abby Maizel et al., Proc. Natl. Acad. Sci., U.S.A., vol. 79, 5998–6002 (1982), and for the latter, see, for example, "Immunochemistry" (Japanese-language publication), edited by Shunsuke Uda, Pages 51–63, published by Nakayama Shoten, 1972). The amounts of these materials may be easily selected experimentally. For example, based on the volume of the medium, about 5 to 20% by volume of human BCGF and about 5 to 100 micrograms/ml-medium of anti-$\mu$ may be used.

In the present invention, the fused cells may be produced, for example, by contacting the human B cells of the human liver cancer patient with the subclone of human lymphoblast cells in a solvent by using a fusion promoter such as Sendai virus (HVJ) or polyethylene glycol or by using an electrofusion apparatus.

For example, the above human B cells and the subclone are placed in an aqueous medium in the presence of the fusion promotor, and the system is made homogenous by optionally stirring it gently. The homogenous system is allowed to stand for a time sufficient to produce a fused cell from one human B cell and one subclone (human B cell), for example for several minutes, to give the desired fused cells. The solvent may be, for example, water, physiological saline, a 5% aqueous solution of dimethyl sulfoxide, or a 5% aqueous solution of glycerol.

The system in which the desired fused cells have been produced are, for example, centrifuged and the cells are harvested. They are dispersed in a suitable medium such as a medium obtained by adding HATO reagent to a RPMI-1640 liquid medium containing 10% calf or bovine fetal serum. The dispersion is dividedly injected into the wells of a microtiter plate at a fixed rate, and cultivated, for example, at 37° C. in the presence of 5% $CO_2$. A medium (RDF) composed of a mixture of RPMI-1640, DME and F-12 (2:1:1) may be used instead of the RPMI-1640 medium mentioned above. The culture fluid in each well is replaced by a fresh one every three days, and the cultivation is continued, for example, for 2 weeks. The formation of fused cells is examined under a microscope. The culture fluids of the wells in which the formation of a fused cell colony is observed are taken. The presence of human immunoglobulin in the culture fluids can be detected by, for example, radioimmunoassay using $^{125}I$, or an enzyme-labelled antibody technique.

The colonies in which the production of human immunoglobulins is observed are transferred to a fresh medium, and cultivated. As a result, the fused cells are proliferated, and fused cell clones can be obtained. As required, by sub-cloning, clones having the ability to produce human immunoglobulins binding specifically to cancer-related antigens such as human liver cancer can be obtained.

In the practice of this embodiment, the techniques described in Glassy, M. C., Handley, H. H., Hagiwara, H. and Royston, I.: Proc. Nat. Acad. Sci., U.S.A., 80, 6327 (1983) and "Koso Kotai Ho" (Enzyme-Labelled Antibody Technique), edited by Keiichi Watanabe, Gakusai Kikaku, pages 33–118 (1956) may be used.

For example, by biopsy, lymphoblasts are taken from the spleen of a healthy person, or lymphatic cells such as lymphocytes, from a patient with myeloma. B cell lymphocytes substantially having no ability to produce immunoglobulins are selected and separated. Thus, human B cells having such sensitivity that they are resistant to 6-thioguanine and ouabain and die in HATO medium can be obtained. For example, the human B cells, HIH/TO1, used in a working example given hereinafter can be obtained by cultivating the aforesaid lymphoblasts in a medium containing 6-thioguanine and ouabain as shown in Referential Example 1 given hereinafter.

The cytobiochemical properties of human/human hybridomas having the ability to produce antigen-specific immunoglobulins, TOH/B9 (FERM BP-1883) and TOH/D5 (FERM BP-1882), produced from human B cells of a human patient with liver cancer and subclone HIH/TO1 (FERM BP-1884) of human lymphoblast cells are described below.

Human/human hybridoma TOH/B9

(1) Human immunoglobulin A (IgA) secreting (producing)

(2) Doubling time: about 37 hours (3) The DNA content is about 2 times, for example 1.5 to 2.5 times, that of normal human lymphocytes.

(4) IgA in (1) above shows bindability to human cell line PLC/PRF/5 (Alexander cells) (liver cancer).

(5) It can be divided and proliferated in HATO medium (medium containing hypoxanthine, amethopterin, thymidine and ouabain).

Human/human hybridoma TOH/D5

(1) Human immunoglobulin G (IgG) secreting (producing)

(2) Doubling time: about 37 hours (3) The DNA content is about 2 times, for example 1.5 to 2.5 times, that of normal human lymphocytes.

(4) IgG in (1) above shows bindability to human cell line PLC/PRF/5 (Alexander cells) or a formalin-fixed paraffin-embedded slice of human liver cancer tissues.

(5) It can be divided and proliferated in HATO medium (medium containing hypoxanthine, amethopterin, thymidine and ouabain).

The relative DNA content (the ratio to the DNA content of normal human lymphocytes) is determined by analysis with a flow cytometer after staining the sample with propidium iodide.

The antigen-specific human immunoglobulins of this invention can be produced by cultivating fused cells derived from human B cells of a human liver cancer patient and a subclone (human B cells) of human lympho-blast cells which have the ability to produce antigen-specific human immunoglobulins, and recovering the antigen-specific human immunoglobulins from the culture broth.

For example, the human/human hybridoma produced as described above is cultivated in a suitable medium such as RPMI-1640 medium containing 10% bovine fetal serum, and a substance containing immunoglobulins binding specifically to a cancer-related antigen such as human liver cancer cells can be obtained from the culture broth. A serum-free medium may be used in the cultivation of the human/human hybridoma, and this is advantageous because it enables the resulting immunoglobulins to be purified easily. Such a serum-free medium is described, for example, in Japanese Laid-Open Patent Publication No. 59183/1987 (Japanese Patent Application No. 192145/1985) filed by the same applicants as the present applicants. If desired the above substance may be purified to form pure immunoglobulins. The purification may be carried out by purification means which can be used in purifying immunoglobulins taken from biological fluids, for example an ammonium sulfate method, affinity chromatography, gel filtration, ion-exchange chromatography and electrophoresis.

In obtaining a substance containing immunoglobulins binding specifically to a cancer-related antigen such as human liver cancer cells or the immunoglobulins from the fusion cell cones or the culture thereof in accordance with this invention, it is advantageous to inoculate an antigenic tissue (such as a cancer tissue) in an animal lacking the ability, or having a very weak ability, to produce immunological substance, such as a nude mouse, maintaining the inoculated tissue, searching a human immunoglobulin (antibody which reacts with the tissue so maintained or returned to the cultivation system, and to separate it.

Other examples of the medium that can be utilized in cultivating the human/human hybridoma include RDF medium composed of a 2:1:1 mixture of RPMI-1640 medium containing 10% bovine fetal serum, Dulbecco medium and HAM medium, and RDF medium containing transferin, insulin, sodium selenite, ethanolamine and beta-mercaptoethanol. The cultivation may be carried out in the presence of 5% $CO_2$ at 37° C.

Examples of the cancer-related antigen-specific human immunoglobulin of the invention which can be obtained as above are immunogloblins obtained by using the aforesaid human/human hybridoma TOH/B9 and human/human hybridoma TOH/D5. Their characteristics are shown below.

Cancer-related antigen-specific human immunoglobulin produced by human/human hybridoma TOH/B9

(a) It is human immunoglobulin A (IgA).

(b) It has a power of binding to human cell line PLC/PRF/5 (Alexander cells) (liver cancer).

(c) It contains a heavy chain having a molecular weight of about 60,000 and a light chain having a molecular weight of about 20,000.

Cancer-related antigen-specific human immunoglobulin produced by human/human hybridoma TOH/D5

(a) It is human immunoglobulin G (IgG).

(b) It shows bindability to human cell line PLC/PRF/5 (Alexander cells) or a human liver cancer tissue.

(c) It consists of H- and L-chains and has a molecular weight of about 150,000.

The human cell line PLC/PRF/5 (Alexander cells) (liver cancer) is freely available from American Type Culture Collection as ATCC CR1, 8024.

The antigen-specific human immunoglobulins of this invention can inhibit proliferation of human cancer cells such as human liver cancer cells or kill them by their own action or by the action of an antibody acting on human cancer cells such as human liver cancer cells. Alternatively, with the aid of complement or T-lymphocytes, they can inhibit proliferation of cancer cells or kill them. Furthermore, they are useful for inhibiting the proliferation, or kill, cancer cells when used in the form of a chemotherapeutic agent-bound human monoclonal antibody, an interferon-bound human monoclonal antibody, a high-molecular toxin-bound human monoclonal antibody, a drug-containing liposome-bound human monoclonal antibody using a cancer-specific antibody produced in great quantities outside the human body as a carrier. When a radioactive x-ray-sensitive substance is bound to the human monoclonal antibody obtained in this invention used as a carrier and administered to a patient with cancer, the monoclonal antibody gather selectively at the cancer cells. This enables detection of a diseased part and can be utilized in radiotherapy. In utilizing the immunoglobulins of the invention against cancer, only a completely monoclonal antibody may be used. It is also possible to create a more effective modified human monoclonal antibody by a chemical method by cutting the antibody into a smaller molecule containing a specific antigen recognizing site, or bonding such a smaller molecule or only the specific antigen recognizing site to a non-specific antigen recognizing site of another antibody, and use the modified human monoclonal antibody.

The following examples illustrate the present invention in greater detail.

REFERENTIAL EXAMPLE 1

Human B cell-lymphoblast cells HIH/TO1

Human B cell-lymphoblast cells WI-L2 ["Journal of the National Cancer Institute", Vol. 46, No. 3, pp. 647–654 (1971)] were cultivated and adapted in a serum-free medium obtained by adding moderate amounts of insulin, transferin, selenium, ethanolamine, beta-mercaptoethanol and bovine serum albumin to a basal medium RDF. The culture broth was inoculated in a 96-well microtiter plate containing the serum-free medium at a rate of 1 cell/well, and subjected to a cloning operation by a limiting dilution method in the presence of 5% $CO_2$ at 37° C. After the lapse of about one month, one clone which did not substantially produce immunoglobulins IgG and IgM in the medium was selected from 50 well where the above cells proliferated.

This selected clone was cultivated and adapted in the same serum-free medium as above containing 0.1 $\mu$M 6-thioguanine. The cultivation was carried out at 37° C. in the presence of 5% $CO_2$. Every time subcultivation was repeated, the concentration of 6-thioguanine was stepwise increased from 0.2 $\mu$M to 0.5, 1, 2, 4, 10, 15 and 20 $\mu$M. Finally, a monoclone replicable in a serum-free medium containing 20 $\mu$M of 6-thioguanine was selected by cloning by the same limiting dilution method as above.

The clone was cultivated in a basal medium RDF containing 1 $\mu$g/ml of N-methyl-N'-nitro-N-nitrosoguanidine (MNNG, a mutating agent) for 3 hours in the presence of 5% $CO_2$ at 37° C. The cells were then washed with the same serum-free medium as above and cultivated and adapted in the same serum-free medium as above containing 20 $\mu$M of 6-thioguanine and ouabain. The cultivation was carried out in the presence of 5% $CO_2$ at 37° C., and every time subcultivation was repeated, the concentration of ouabain was increased stepwise from 0.1 $\mu$M to 0.2, 0.5, 1 and 5 $\mu$M. Finally, a monoclone capable of replicating in a serum-free medium containing 20 $\mu$M 6-thioguanine and 5 $\mu$M ouabain was selected by cloning by the same limiting dilution method as above to give HIH/TO1.

EXAMPLE 1

At the time of operation, lymph nodes in the periphery of the cancer tissue was obtained from a patient with liver cancer, and cut to fine pieces by scissors. The lymphocytes inside the lymph nodes were dispersed in RDF medium (composed of a 2:1:1 mixture of RPMI-1640, DME and F-12). The dispersion was then filtered by using a double-layered gauze to remove the fat layer. The cells (lymphocytes > 80%) in the filtrate were collected by a centrifugal method [a human lymphocyte fraction containing human B cell donor (donor B cells)]. The lymphocyte fraction was frozen (−130° C.) in RDF medium containing 20% of bovine fetal serum and 10% of dimethyl sulfoxide an stored until the day of cell fusion.

$1.0 \times 10^7$ donor B cells were cultivated at 37° C. in the presence of 5% $CO_2$ in RDF medium containing 5% human BCGF (B cell growth factor produced by Cellular Products, Inc. and Biotech Research Labs.) and 20 $\mu$g/ml goat anti-human IgM (produced by Cappel Company) antibody, and seven days later, centrifuged at 100 G for 15 minutes to collect donor B cells, which were then washed once with RDF medium.

Then, the donor lymphocytes $(1.0 \times 10^7)$ and human parent B cells (HIH/TO1) substantially lacking the ability to produce immunoglobulins $(1.0 \times 10^7)$ were mixed and fused in the presence of 50% polyethylene glycol 1500. The produce was centrifuged at 30 G for 15 minutes to remove polyethylene glycol, and freshly, RDF medium containing 10% bovine fetal serum and hypoxanthine, amethopterin, thymidine and ouabain (HATO) were added. The culture fluid containing these cells was injected into a 96-well microtiter plate at a rate of 200 microliters (containing $1.5 \times 10^5$ cells) per well. Four weeks later, the plate was incubated in an incubator at 37° C. in the presence of 5% $CO_2$. During this time, the RDF medium containing HATO and 10% bovine fetal serum was replaced once in 4 to 5 days. The parent B cells (HIH/TO1) cannot survive in the presence of amethopterin because it lacks hypoxanthine phosphoribosyltransferase. The lymphocytes cannot proliferate and survive for an extended period of time in an ordinary medium, such as RDF containing 10% bovine fetal serum, and moreover, die in the presence of ouabain. Accordingly, cells which proliferated for an extended period of time in a medium containing HATO were the fused cells of the lymphocytes and the parent B cells. After cultivation for 4 weeks, five hybridomas were obtained. It was determined by an enzyme-labelled antibody method whether these hybridomas produced human immunoglobulins. This method will be described below.

An anti-human immunoglobulin antibody (antihuman Ig antibody) (50 µl) was added dropwise to a microtiter plate and maintained at 37° C. for 1 hour to adsorb it on the plate. The plate was washed three times with 10 mM PBS (gelatin buffer) containing 0.3% gelatin, and then a 5% solution of bovine serum albumin was added dropwise (200 microliters) to the plate and the plate was maintained at 37° C. for 0.5 hour to adsorb it on the plate. The plate was washed three times with the gelatin buffer to remove the unadsorbed material. Then, an assay solution (culture supernatant) was added dropwise (50 microliters) and reacted at 37° C. for 1 hour. The plate was then washed three times with the gelatin buffer. Peroxidase-conjugated anti-human Ig antibody (50 microliters) was added dropwise and reacted at 37° C. for 30 minutes to bind it to the human Ig in the culture supernatant (enzyme-labelled antibody technique). The plate was washed three times with the gelatin buffer, and a substrate solution containing hydrogen peroxide and o-phenylenediamine was added and reacted for 10 minutes in a dark chamber. 5N $H_2SO_4$ (50 microliters) was added to stop the reaction. When the peroxidase-conjugated goat anti-human Ig antibody remained on the microtiter plate, namely when the human Ig bound to it remained, a yellow substrate reaction product having an absorption at 490 nm was produced. The amount of the product was measured by using an absorbance meter to determine the amount of the human Ig contained in the supernatant of the hybridoma culture. When no human Ig existed in the supernatant of the hybridoma culture, the peroxidase-conjugated goat anti-human Ig antibody was washed away in the washing step.

By using the above measurement method, it was determined that three out of five hybridoma clones produced antibodies. The clone which produced human IgA was named TOH/B9, and the clone which produced human IgG was named TOH/D5.

Four weeks later, each of the hybridomas was inoculated in a 24-well microtiter plate at a rate of 2 ml per well, and the cultivation was continued further for one week. The supernatant of the culture was collected, and the specificity of the Ig produced from the human hybridoma to various cell lines or cancer tissues was examined (ig having a fixed character or Ig having a specific character). The method will be described below.

Various cell lines (available from ATCC) were each cultivated in a medium prepared by adding 10% bovine fetal serum to DF medium (DME:F-12=1:1). When the number of the cells reached $5 \times 10^6$ to $1 \times 10^7$, the cells were removed from the bottom of the Petri dish using trypsin, and by centrifugation, the cells were collected and well washed with the culture medium. A fixed number ($10^5$/100 microliters) of the cells was injected into each well of a 96-well microtiter plate and maintained overnight at 37° C. to adsorb them on the plate. Then, a 3% solution of glutaraldehyde (50 microliters) was added dropwise and maintained at 37° C. for 20 minutes to fix the cells. The cells were dropped off by a centrifugal method (200 G, 10 minutes), and the plate was washed with a gelatin buffer three times. A 1% solution of bovine serum albumin (200 microliters) was added dropwise and maintained at 37° C. for 1 hour to adsorb it on the plate. The plate was washed three times with a gelatin buffer to remove the unadsorbed material. Then, an assay solution (the culture supernatant) was added dropwise in an amount of 50 microliters on the cells and reacted at 37° C. for 1 hour. The plate was washed with a gelatin buffer three times, and subsequently, 50 microliters of peroxidase-conjugated anti-human Ig antibody was added dropwise and reacted at 37° C. for 30 minutes. The plate was washed with a gelatin buffer three times. The amount of human Ig in the culture fluid which bound to the cells was measured by the method described hereinabove with regard to the enzyme-labelled antibody technique, and its specificity to the cell lines was examined.

Furthermore, a slice of the cancer tissue fixed with formalin and then embedded in paraffin was treated with an ethanol solution to remove the paraffin, and an assay solution (the culture supernatant) was added, and the specificity of Ig produced by the hybridoma was examined by using a commercial kit "Vectastain ABC kit" made by Vector Laboratories Ltd.

It was consequently found that IgA produced by TOH/B9 had a power of binding to cell line PLC/PRF/5 (ATCC CRL 8024) derived from human liver cancer, IgG produced by TOH/D5 was found to have a power of binding to human cell line PLC/PRF/5 (Alexander ells) or a human liver cancer tissue.

This shows that since the donor B cells were taken from a patient having liver cancer, the clone of the hybridoma produced by cell fusion and having self-replicability produces a monoclonal antibody having the same character as the donor B cell and a specific antigen binding site.

Furthermore, to determine that the cells obtained by cell fusion are hybridomas, the DNA content of the cells was examined by the following method.

The cell culture wa put in a centrifugal tube, and by centrifugal treatment, the supernatant was removed. The cells was then fixed with a 70% ethanol solution at 4° C. for more than 30 minutes. The supernatant was removed by centrifugal treatment, and a solution of RNase was added. The mixture was gently shaken to decompose RNA. After reaction at 37° C. for 30 minutes, the reaction mixture was washed twice with distilled water. Pripidium iodide (PI) was added, and the cells were stained with it at room temperature for 20 minutes. They were washed with distilled water twice, and diluted with distilled water. Analysis by a cell sorter showed that in both TOH/D5 and TOH/B9, the DNA content was about twice that of the parent human B cells (HIH/TO1). Thus, these cells were determined to be hybridomas.

Three weeks later, HATO was removed from the culture media of the hybridomas and the hybridomas were cultivated in a medium composed of RDF and 10% bovine fetal serum. When $1.0 \times 10^6$ cells grew on the media, TOH/B9 produced about 1.3 micrograms/ml of human IgA, and TOH/D5 produced about 0.15 microgram/ml of IgG.

What we claim is:

1. The antigen-specific human immunoglobulin which is produced by human/human hybridoma TOH/B9 FERM BP-1883 and which has the following biochemical properties:

(a) it is human immunoglobulin (IgA), and (b) it specifically binds to human cell line PLC/PRF/5 (Alexander cells) derived from human liver cancer.

2. The antigen-specific human immunoglobulin which is produced by human/human hybridoma TOH/D5 FERM BP-1882 and which has the following biochemical properties:
   (a) it is human immunoglobulin G (IgG), and
   (b) it specifically binds to human cell line PLC/PRF/5 (Alexander cells) or a human liver cancer tissue.

3. A human/human hybridoma TOH/B9 FERM BP-1883 which produces antigen-specific human immunoglobulin, said hybridoma being a human/human fused cell strain derived from a human B cell taken from a human patient with liver cancer and a subclone of a human lymphoblast cell strain.

4. A human/human hybridoma TOH/D5 FERM-BP-1882 which produces antigen-specific human immunoglobulin, said hybridoma being a human/human fused cell strain derived from a human B cell taken from a human patient with liver cancer and a subclone of a human lymphoblast cell strain.

5. The human/human hybridoma of claim 3 which has the following cytobiochemical properties (1) to (5):
   (1) it secretes (produces) a human immunoglobulin A (IgA),
   (2) it has a doubling time of about 37 hours,
   (3) it has a DNA content about twice as large as that of a normal human lymphocyte,
   (4) the IgA mentioned in (1) above shows bindability to human cell line PLC/PRF/5 (Alexander cells) (derived from human liver cancer), and
   (5) it can be divided and proliferated in a medium containing hypoxanthine, amethopterin, thymidine and ouabain.

6. The human/human hybridoma of claim 4 which has the following cytobiochemical properties (1) to (5):
   (1) it secretes (produces a human immunoglobulin G (IgG),
   (2) it has a doubling time of about 37 hours,
   (3) it has a DNA content about twice as large as that of a normal human lymphocyte,
   (4) the IgG mentioned in (1) above shows bindability to human cell line PLC/PRF/5 (Alexander cells) or a human liver cancer tissue, and
   (5) it can be divided and proliferated in a medium containing hypoxanthine, amethopterin, thymidine and ouabain.

7. The antigen-specific human immunoglobulin of claim 4 or 5, wherein said immunoglobulin is bound to an agent selected from the group consisting of a chemotherapeutic agent, interferon, high-molecular weight toxin, anti-cancer drug-containing liposome, and radioactive x-ray sensitive agent.

* * * * *